United States Patent
Ueno et al.

(10) Patent No.: US 7,129,272 B2
(45) Date of Patent: Oct. 31, 2006

(54) APOPTOSIS INHIBITOR

(75) Inventors: Ryuji Ueno, Montgomery, MD (US); Yukihiko Mashima, Tokyo (JP)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 09/816,655

(22) Filed: Mar. 26, 2001

(65) Prior Publication Data

US 2002/0025985 A1    Feb. 28, 2002

Related U.S. Application Data

(60) Provisional application No. 60/191,755, filed on Mar. 20, 2000.

(51) Int. Cl.
*A61K 31/215*    (2006.01)

(52) U.S. Cl. .................. 514/530; 514/573; 514/912

(58) Field of Classification Search ................ 514/530, 514/573, 912
See application file for complete search history.

(56) References Cited

U.S. PATENT DOCUMENTS

| | | | |
|---|---|---|---|
| 5,073,569 A | 12/1991 | Ueno et al. .................. 514/530 |
| 5,166,174 A | 11/1992 | Ueno et al. .................. 514/530 |
| 5,212,324 A | 5/1993 | Ueno .......................... 554/118 |
| 5,221,763 A | 6/1993 | Ueno et al. .................. 560/121 |
| 5,739,161 A | 4/1998 | Ueno .......................... 514/530 |
| 6,087,395 A | 6/2000 | Watanabe et al. ............ 514/530 |

FOREIGN PATENT DOCUMENTS

| | | |
|---|---|---|
| EP | 0 308 135 A | 3/1989 |
| EP | 0 435 443 A2 | 7/1991 |

OTHER PUBLICATIONS

Shahinfar, S. et al., "A pathologic study of photoreceptor cell death in retinal photic injury", Current Eye Research, vol. 10, No. 1, 1991.

Aoyama-Hayashi, E. et al., $PGE_1$ in hibited daunorubicin-induced apoptosis of human leukemia cell line, U937, Japanese Journal of Inflammation, vol. 18, No. 5, Sep. 1998.

Duvall, E. et al., "Death and the cell", Immunology Today, vol. 7, No. 4, 1986.

Trauth, B. et al., "Monoclonal Antibody-Mediated Tumor Regression by Induction of Apoptosis", Science, vol. 245, Jul. 21, 1989.

Patent Abstracts of Japan vol. 2000, No. 9, Oct. 13, 2000 & JP 2000 169394 A (Yoshitomi Pharmaceut. Ind. Ltd.).

Patent Abstracts of Japan vol. 1997, No. 2, Feb. 28, 1997 & JP 08 277222A (Green Cross Corp: The) Oct. 22, 1996 abstract.

Feely W. F. Et al., "Normal Phase High Performance Liquid Chromatography of some Prostaglandin B-1 Derivatives" Joruanl of Liquid Chromatography, vol. 12, No. 4, 1989, pp. 515-528, XP000062725 issn: 0148-3919; p. 516, paragraph 2, p. 517.

Katzenschlager R., et al. "Synergism between PGE1-metabolites(13,14-dihydro-prostaglandin E1, 15-keto prostaglandin E1, 15-keto-13,14-dihydro-prostaglandin E1) and nitric oxide (NO) on platelet aggregation" Prostaglandins Leukot Essent Fatty Acids. Mar. 1992, 45(3)L 207-10.

*Primary Examiner*—Zohreh Fay
(74) *Attorney, Agent, or Firm*—Sughrue Mion, PLLC

(57) ABSTRACT

Disclosed is a method for treatment of a subject having a disease or condition associated with apoptosis, which comprises administering to the subject an effective amount of a 15-keto-prostaglandin compound represented by the following formula (I):

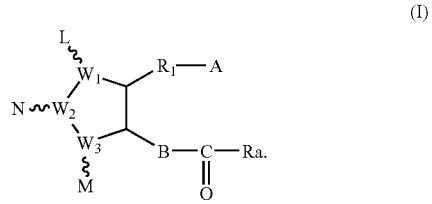

(I)

18 Claims, No Drawings

APOPTOSIS INHIBITOR

CROSS REFERENCE TO RELATED APPLICATION

This application claims the benefit of priority based on U.S. Provisional Application No. 60/191,755 filed Mar. 24, 2000 under the provision of 35 U.S.C. § 111(b), pursuant to 35 U.S.C. §119(e)(1).

TECHNICAL FIELD

The present invention relates to a new use of 15-keto prostaglandin compound as an apoptosis inhibitor.

BACK GROUND OF THE INVENTION

Apoptosis is a kind of genetically programmed cell death. Morphologically apoptosis of a cell occurs along with the process as follows: condensation of the nucleus of the cell; cell shrinkage; cytoplasmic vacuolation and cell surface smoothing; enlargement of intercellular space; release of the cell from the pericellular region; fragmentation of the cell (to provide apoptosis body) and phagocytosis of the fragment by macrophage or the like. Biochemically, nucleosomal DNA is cleaved by endonuclease into 180–220 bp DNA fragments (Immunology Today 7:115–119, 1986; Science 245:301–305, 1989, the cited references are herein incorporated by reference.)

Today, it has been revealed that apoptosis plays a role not only in physiological cell death concerning generation/differentiation and turn over of normal tissues and cells, but also in some conditions or diseases such as nerve cells death by ischemia after cerebral infarction, cell death by radioisotope or anti cancer agent, cell death by a toxin or virus infection, lymphocytopenia due to virus infection such as AIDS, autoimmune disease, Alzheimer disease and inflammatory. Further, apoptosis plays a role in photoreceptor cell death observed in light induced retinal photic injury (Current Eye Research Vol. 10 No. 1:47–59, 1991, the cited reference is herein incorporated by reference). Accordingly, development of new apoptosis controlling drugs (that is, apoptosis inhibitor and apoptosis inducer) are expected to provide new type of drugs with novel mode of action useful in a variety of fields such as immunology, cerebral nerve system, optic nerve system, cancer, aging and the like.

Prostaglandins (hereinafter, referred to as PG(s)) are members of class of organic carboxylic acids, which are contained in tissues or organs of human or most other mammalian, and exhibit a wide range of physiological activity. PGs found in nature (primary PGs) generally have a prostanoic acid skeleton as shown in the formula (A):

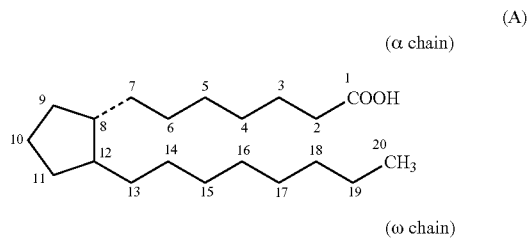

(A)

On the other hand, some of synthetic analogues have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

subscript 1: 13,14-unsaturated-15-OH subscript 2: 5,6- and 13,14-diunsaturated-15-OH subscript 3: 5,6-, 13,14- and 17,18-triunsaturated-15-OH.

Further, the PGFs are classified, according to the configuration of the hydroxy group at position 9, into α type (the hydroxy group is of a α-configuration) and β type (the hydroxy group is of a β-configuration).

$PGE_1$, $PGE_2$ and $PGE_3$ are known to have vasodilation, hypotension, gastric secretion decreasing, intestinal tract movement enhancement, uterine contraction, diuretic, bronchodilation and anti ulcer activities. $PGF_{1\alpha}$, $PGF_{2\alpha}$ and $PGF_{3\alpha}$ have been known to have hypertension, vasoconstriction, intestinal tract movement enhancement, uterine contraction, lutein body atrophy and bronchoconstriction activities.

In addition, some 15-keto prostaglandins (i.e. those having an oxo group at position 15 in place of the hydroxy group) and 13,14-dihydro-15-keto-prostaglandins are known as substances naturally produced by enzymatic actions during in vivo metabolism of primary PGs. 15-keto PGs have been disclosed in the specification of U.S. Pat. Nos. 5,073,569, 5,166,174, 5,221,763, 5,212,324 and 5,739,161. (These cited references are herein incorporated by reference.)

As apoptosis inhibitors, Interleukine-1 converting enzyme inhibitor and basic fibroblast growth factor (bFGF) have been known. Further, isocarbacycline derivative inhibits apoptosis of nerve cells (European patent application Laid Open No. 911314, the cited reference is herein incorporated by reference), and prostaglandin E, inhibits daunorbicin-induced apoptosis of human leukaemic cells. (Japanese Journal of Inflammation Vol. 18, No. 5:369–376, 1988; the cited reference is herein incorporated by reference).

SUMMARY OF THE INVENTION

An object of the present invention is to provide an apoptosis inhibitor, which is useful for treatment of various conditions and diseases associated with apoptosis.

The inventors have studied on bioactivity of 15-keto prostaglandin compounds and found that 15-keto-prostaglandin compounds express a significant apoptosis inhibiting activity, and achieved to the invention. That is, the present invention provides an apoptosis inhibitor composition comprising a 15-keto-prostaglandin compound as an active ingredient.

In the present invention, the "15-keto-prostaglandin compounds" (hereinafter, referred to as "15-keto-PG compounds") may include any of derivatives or substitution compounds of a compound having an oxo group at 15-position of the prostanoic acid skeleton instead of the hydroxy group, irrespective of the configuration of the five membered ring, the number of double bonds, presence or absence of a substituent, or any other modification in the α or ω chain.

The nomenclature of the 15-keto-PG compounds used herein is based on the numbering system of prostanoic acid represented in the above formula (A).

The formula (A) shows a basic skeleton of the C-20 PG compound, but the 15-keto-PG compounds in the present invention are never limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, compounds are named as substitution compounds having respective substituents at position 21. Stereochemistry of the compounds is the same as that of the above formula (A) unless otherwise specified.

In general, each of PGD, PGE and PGF represents a PG compound having hydroxy groups at positions 9 and/or 11, but in the present specification they also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy compound.

As stated above, the nomenclature of 15-keto-PG compounds is based on the prostanoic acid skeleton. However, in case the compound has a similar partial construction as a prostaglandin, the abbreviation of "PG" may be used. Thus, a PG compound of which a chain is extended by two carbon atoms, that is, having 9 skeletal carbon atoms in the a chain is nominated as 2-decarboxy-2-(2-carboxyethyl)-15-keto PG compound. Similarly, a compound having 11 skeletal carbon atoms in the a chain is as 2-decarboxy-2-(4-carboxybutyl)-15-keto-PG compound. Further, a 15-keto-PG compound of which ω-chain is extended by two carbon atoms; that is, having 10 skeletal carbon atoms in the ω-chain is nominated as 15-keto-20-ethyl-PG compound. These compounds, however, may also be named according to the IUPAC naming system.

The 15-keto-PG compound used in the present invention may be any derivative of a PG insofar as having an oxo group at position 15 in place of the hydroxy group, and may further include compounds having one double bond at position 13-14 (15-keto-PG type 1 compound), two double bonds at positions 13-14 and 5-6 (15-keto-PG type 2 compound), or three double bonds at positions 13-14, 5-6 and 17-18 (15-keto-PG type 3 compound) and 13,14-dihydro-15-keto-PG compounds wherein the double bond at position 13-14 is converted to single bond.

Typical examples of the compounds used in the present invention include 15-keto-PG type 1, 15-keto-PG type 2, 15-keto-PG type 3, 13,14-dihydro-15-keto-PG type 1, 13,14-dihydro-15-keto-PG type 2, 13,14-dihydro-15-keto-PG type 3 and the derivatives thereof.

Examples of the substitution compounds or derivatives include a 15-keto-PG compound of which carboxy group at the end of a chain is esterified; a compound of which α chain is extended; physiologically acceptable salt thereof; an unsaturated derivative having a double bond at 2-3 position or a triple bond at position 5-6, a PG compound having substituent(s) at position(s) 3, 5, 6, 16, 17, 18, 19 and/or 20; and a PG compound having lower alkyl or a hydroxy (lower) alkyl group at position 9 and/or 11 in place of the hydroxy group.

According to the present invention, preferred substituents at positions 3, 17, 18 and/or 19 include alkyl having 1–4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include halogen atoms such as chlorine and fluorine. Preferred substituents at position 20 include saturated or unsaturated lower alkyl such as $C_{1-4}$ alkyl, lower alkoxy such as $C_{1-4}$ alkoxy, and lower alkoxy alkyl such as $C_{1-4}$ alkoxy-$C_{1-4}$ alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at positions 9 and 11 may be α, β or a mixture thereof.

Further, the above derivatives may be compounds having an alkoxy, cycloalkyl, cycloalkyloxy, phenoxy or phenyl group at the end of the ω-chain where the chain is shorter than the primary PGs.

Especially preferred compounds include a 13,14-dihydro-15-keto-PG compound which has a single bond at position 13-14; a 15-keto-16 mono or di-halogen PG compound which has one or two halogen atoms such as chlorine and fluorine at position 16; a 2-decarboxy-2-(2-carboxyethyl)-15-keto-PG compound in which skeletal carbon of a chain is extended by two carbon atoms; and a 15-keto-PGE compound which has an oxo group at position 9 and a hydroxy group at position 11 of the five memberd ring.

A preferred compound used in the present invention is represented by the formula (I):

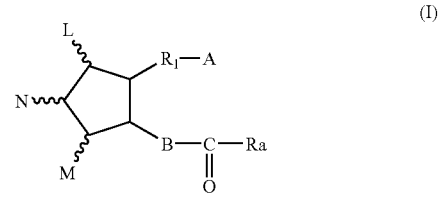

wherein L, M and N are hydrogen, hydroxy, halogen, lower alkyl, hydroxy(lower)alkyl or oxo, wherein at least one of L and M is a group other than hydrogen, and the five-membered ring may have at least one double bond;

A is —CH₂OH, —COCH₂OH, —COOH or a functional derivative thereof;

B is —CH₂—CH₂—, —CH=CH— or —C≡C—;

R₁ is a divalent saturated or unsaturated lower-medium aliphatic hydrocarbon residue, which is unsubstituted or substituted with halogen, oxo, aryl or heterocyclic; and Ra is a saturated or unsaturated lower-medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic or heterocyclic-oxy; cyclo(lower)alkyl; cyclo(lower)alkyloxy; aryl; aryloxy; heterocyclic; or heterocyclic-oxy.

A group of particularly preferable compounds among the above-described compounds is represented by the general formula (II):

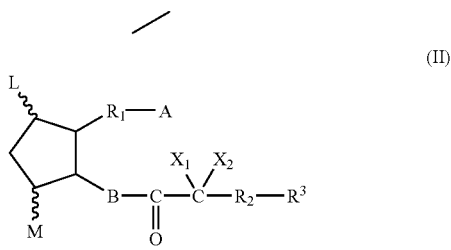

(II)

wherein L and M are hydrogen, hydroxy, halogen, lower alkyl, hydroxy(lower)alkyl or oxo, wherein at least one of L and M is a group other than hydrogen, and the five-membered ring may have at least one double bond;

A is —$CH_2OH$, —$COCH_2OH$, —COOH or a functional derivative thereof;

B is —$CH_2$—$CH_2$—, —CH=CH— or —C≡C—;

$X_1$ and $X_2$ are hydrogen, lower alkyl or halogen;

$R_1$ is a divalent saturated or unsaturated lower-medium aliphatic hydrocarbon residue, which is unsubstituted or substituted with halogen, oxo, aryl or heterocyclic;

$R_2$ is a single bond or lower alkylene; and $R_3$ is lower alkyl, lower alkoxy, cyclo(lower)alkyl, cyclo(lower)alkyloxy, aryl, aryloxy, heterocyclic or heterocyclic-oxy.

In the above formula, the term "unsaturated" in the definitions for $R_1$ and $R_a$ is intended to include at least one or more double bonds and/or triple bonds that are isolatedly, separately or serially present between carbon atoms of the main and/or side chains. According to the conventional nomenclature, an unsaturated bond between two serial positions is represented by denoting the lower number of the two positions, and an unsaturated bond between two distal positions is represented by denoting both of the positions.

The term "lower-medium aliphatic hydrocarbon" means a hydrocarbon having a straight or branched chain of 1 to 14 carbon atoms, wherein the side chain has preferably 1 to 3 carbon atoms. The preferred $R_1$ has 1 to 10, especially 6 to 10 carbon atoms, and the preferred $R_2$ has 1 to 10, especially 1 to 8 carbon atoms.

The term "halogen" includes fluorine, chlorine, bromine and iodine.

The term "lower" means a group having 1 to 6 carbon atoms unless otherwise specified.

The term "lower alkyl" means a straight- or branched-chain saturated hydrocarbon group having 1 to 6 carbon atoms, for example, methyl, ethyl, propyl, isopropyl, butyl, isobutyl, t-butyl, pentyl and hexyl.

The term "lower alkoxy" means a lower alkyl-O— wherein the lower alkyl is as described above.

The term "hydroxy(lower)alkyl" means an alkyl as described above, which is substituted with at least one hydroxy group, for example, hydroxymethyl, 1-hydroxyethyl, 2-hydroxyethyl and 1-methyl-1-hydroxyethyl.

The term "lower alkanoyloxy" means a group represented by the formula RCO—O—, wherein RCO— is an acyl formed by oxidation of a lower alkyl as described above, for example, acetyl.

The term "cyclo (lower) alkyl" means a group formed by cyclization of a lower alkyl group containing 3 or more carbon atoms as described above, for example, cyclopropyl, cyclobutyl, cyclopentyl and cyclohexyl.

The term "cyclo(lower)alkyloxy" means a group represented by the formula cycloalkyl-O—, wherein cycloalkyl is as described above.

The term "aryl" includes optionally substituted aromatic hydrocarbon ring, preferably monocyclic group, for example, phenyl, tolyl and xylyl. Examples of the substituents include halogen and halogen substituted lower alkyl group, wherein halogen atom and lower alkyl group are as described above.

The term "aryloxy" means a group represented by the formula ArO—, wherein Ar is an aryl group as described above.

The term "heterocyclic" includes mono- to tri-cyclic, preferably monocyclic heterocyclic group which is 5 to 14, preferably 5 to 10 membered ring having optionally substituted carbon atom and 1 to 4, preferably 1 to 3 of 1 or 2 kinds of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazyl, pyrimidyl, pyrazyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, puryl, quinazolinyl, carbazolyl, acridinyl, phenanthridinyl, benzimidazolyl, benzimidazolonyl, benzothiazolyl and phenothiazinyl. Examples of the substituent in this case include halogen and halogen substituted lower alkyl group, wherein halogen atom and lower alkyl group are as described above.

The term "heterocyclic-oxy" means a group represented by the formula HcO—, wherein Hc is a heterocyclic group as described above.

The term "functional derivative" of A includes salts (preferably pharmaceutically acceptable salts), ethers, esters and amides.

Examples of suitable "pharmaceutically acceptable salts" include commonly used nontoxic salts such as salts with inorganic bases, for example, alkali metal salts (sodium salt, potassium salt and the like); alkaline earth metal salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, lysine salt, procaine salt and caffeine salt); basic amino acid salts (such as arginine salt and lysine salt); tetraalkyl ammonium salts and the like. These salts may be manufactured from, for example, corresponding acids and bases in accordance with a conventional manner or by the salt exchange process.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; medium or higher alkyl ethers such as octyl ether, diethylhexyl ether, lauryl ether and cetyl ether; unsaturated ethers such as oleyl ether and linolenyl ether; lower alkenyl ethers such as vinyl ether and allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl esters such as hydroxyethyl ester; and lower alkoxy(lower)alkyl esters such as methoxymethyl ester and 1-methoxyethyl ester, and as well as, for example, optionally substituted aryl esters such as phenyl ester, tolyl ester, t-butylphenyl ester, salicyl ester, 3,4-dimethoxyphenyl ester and benzamidephenyl ester; and aryl(lower)alkyl esters such as benzyl ester, trityl ester and benzhydryl ester. Examples of amides include mono- or di-lower alkyl amides such as methylamide, ethylamide and dimethylamide; aryl amides such as anilide and toluidide; and alkyl or aryl sulfonyl amides such as methylsulfonyl amide, ethylsulfonyl amide and tolylsulfonyl amide.

Preferred examples of L and M include hydroxy and oxo and especially, M is hydroxy and L is oxo which provide a 5-membered ring structure of, so called, PGE type.

Preferred examples of A-group include —COOH and its pharmaceutically acceptable salts, esters and amides.

Preferred example of B is —CH$_2$—CH$_2$— which provides the structure of so-called, 13,14-dihydro type.

Preferred example of X$_1$ and X$_2$ is that at least one of them is halogen, more preferably, both of them are halogen, especially, fluorine that provides a structure of, so called 16,16-difluoro type.

Preferred R$_1$ is a hydrocarbon containing 1–10 carbon atoms, preferably 6–10 and more preferably 8 carbon atoms.

Examples of R$_1$ include, for example, the following groups:
—CH$_2$—CH$_2$—CH$_2$—CH$_2$—CH$_2$—CH$_2$—,
—CH$_2$—CH=CH—CH$_2$—CH$_2$—CH$_2$—,
—CH$_2$—CH$_2$—CH$_2$—CH$_2$—CH=CH—,
—CH$_2$—C≡C—CH$_2$—CH$_2$—CH$_2$—,
—CH$_2$—CH$_2$—CH$_2$—CH$_2$—CH(CH$_3$)—CH$_2$
—CH$_2$—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—CH$_2$—,
—CH$_2$—CH$_2$—CH$_2$—CH$_2$—CH$_2$—CH$_2$—CH=CH—,
—CH$_2$—C≡C—CH$_2$—CH$_2$—CH$_2$—CH$_2$—CH$_2$—,
—CH$_2$—CH$_2$—CH$_2$—CH$_2$—CH$_2$—CH$_2$—CH(CH$_3$)—CH$_2$—, Preferred Ra is a hydrocarbon containing 1–10 carbon atoms, more preferably, 1–8 carbon atoms. Ra may have one or two side chains having one carbon atom.

The configuration of the ring and the α- and/or ω chains in the above formulae (I) and (II) may be the same as or different from those of the primary PGs. However, the present invention also includes a mixture of a compound having a primary type configuration and a compound of a non-primary type configuration.

Typical examples of the compounds used in the present invention include 2-decarboxy-2-(carboxy lower alkyl)-15-keto-PG compounds, especially, 2-decarboxy-2-(2-carboxy-ethyl)-15-k to-PG compound and 2-d carboxy-2-(4-carboxy-butyl)-15-keto PG compound and 5-fluoro, 6-keto, 11-dehydroxy, 16-fluoro, 16-methyl, 17-fluoro, 17-methyl, 18-methyl, 19-methyl, 20-methyl, 20-ethyl, 20-propyl and 18,19,20-trinor-17-phenyl derivatives thereof.

When a 15-keto-PG compound of the present invention has a saturated bond at position 13-14, the compound may be in the keto-hemiacetal equilibrium by formation of a hemiacetal between hydroxy at position 11 and keto at position 15.

For example, it has been revealed that when both of X$_1$ and X$_2$ are halogen atoms, especially, fluorine atoms, the compound contains a tautomeric isomer, bicyclo-nonane compound of the formula (III)

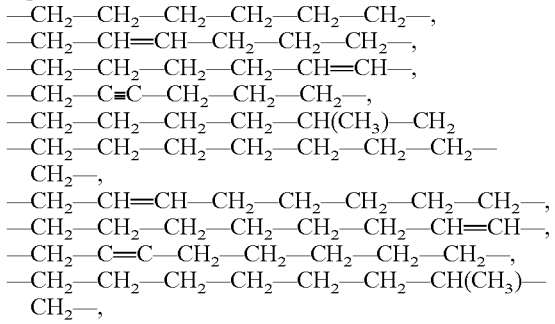

wherein, A is —CH$_2$OH, —COCH$_2$OH, —COOH or a functional derivative thereof;
X$_1$' and X$_2$' are hydrogen, lower alkyl or halogen;
Y is

wherein R$_4$' and R$_5$' are hydrogen, hydroxy, halogen, lower alkyl, lower alkoxy or hydroxy(lower)alkyl, wherein R$_4$' and R$_5$' are not hydroxy and lower alkoxy at the same time;
R$_1$ is a divalent saturated or unsaturated lower-medium aliphatic hydrocarbon residue, which is unsubstituted or substituted with halogen, oxo, aryl or heterocyclic;
R$_2$' is a saturated or unsaturated lower-medium aliphatic hydrocarbon residue, which is unsubstituted or substituted with halogen, oxo, hydroxy, lower alkoxy, lower alkanoyloxy, lower cycloalkyl, lower cycloalkyloxy, aryl, aryloxy or heterocyclic; lower cycloalkyl; lower cycloalkyloxy; aryl; aryloxy; heterocyclic; or heterocyclicoxy;
R$_3$' is hydrogen, lower alkyl, lower cycloalkyl, aryl or heterocyclic.

If such tautomeric isomers as above are present, the proportion of both tautomeric isomers varies with the structure of the rest of the molecule or the substituent present. Sometimes one isomer may be present predominantly in comparison with the other. However, it is to be appreciated that the compounds used in the invention include both isomers. Further, while the compounds used in the invention may be represented by a structure formula or name based on keto-form regardless of the presence or absence of the isomers, it is to be noted that such structure or name does not intend to eliminate the hemiacetal type of compounds.

In the present invention, any of the individual tautomeric isomers and mixtures thereof, or optical isomers and mixtures thereof, racemic mixtures and other isomers such as steric isomers may be used in the same purpose.

Some of the compounds used in the present invention may be prepared by the method disclosed in U.S. Pat. Nos. 5,073,569, 5,166,174, 5,221,763, 5,212,324 and 5,739,161 and U.S. patent application Ser. No. 09011218 (these cited references are herein incorporated by reference).

The compounds used in the present invention may be used as drugs for animals and human beings and usually applied systemically or topically by such methods as ophthalmic instillation, oral administration, intravenous injection (including infusion), subcutaneous injection, intra rectal administration, intra vaginal administration and the like. Especially, ophthalmic instillation is preferable. The dosage may vary depending on the strain of the patient, i.e. particular animal or human, age, body weight, symptom to be treated, desired therapeutic effect, administration route, term of treatment and the like. A satisfactory effects may be obtained by topical administration of the compound at the amount of 0.01–100 µg/eye, or by systemic administration 2–4 times per day or continuous administration at the amount of 0.001–500 mg/kg per day.

Examples of ophthalmic compositions of the present invention include ophthalmic solution and ointment. The ophthalmic solution may be prepared by dissolving the active ingredient into sterilized aqueous solution such as saline or buffer. A powder composition for ophthalmic solution to be dissolved before use may also be used. The ophthalmic ointment may be prepared by mixing the active ingredient with ointment base.

Examples of solid compositions for oral administration include tablets, troches, sublingual tablets, capsules, pills, powders, granules and the like. The solid composition may be prepared by mixing one or more active ingredients with at least one inactive diluent, e.g. lactose, mannitol, glucose, hydroxypropyl cellulose, fine crystalline cellulose, starch, polyvinyl pyrrolidone and magnesium aluminometasilicate. The composition may further contain additives other than the inactive diluent, for example, lubricants e.g., magnesium stearate, a disintegrator e.g. cellulose calcium gluconates, stabilizers e.g. $\alpha$-, $\beta$- or $\gamma$-cyclodextrin, ether cyclodextrins, e.g. dimethyl-$\alpha$-, dimethyl-$\beta$-, trimethyl-$\beta$- or hydroxypropyl-$\beta$-cyclodextrins, branched cyclodextrins, e.g. glucosyl- or maltosyl-cyclodextrins, formyl cyclodextrin, sulfur-containing cyclodextrin, misoprotol or phospholipids. When a cyclodextrin is used as a stabilizer, the active ingredient may form an inclusion compound with the cyclodextrin to improve the stability. The stability may also be improved by including the ingredient in liposome made from phospholipid. Tablets and pills may be coated with an enteric or gastroenteric film e.g. white sugar, gelatin, hydroxypropylcellulose, hydroxypropylmethyl cellulose phthalates and the like, if necessary. They may be covered with two or more layers. Additionally, the composition may be in the form of capsules made from an easily degradable material such as gelatin. Sublingual tablet is preferable, when an immediate effect is desired.

Base of the composition may be glycerin, lactose and the like. Examples of liquid compositions for oral administration include emulsions, solutions, suspensions, syrups, elixirs and the like. Said compositions may further contain a conventionally used inactive diluent e.g. purified water or ethyl alcohol. The composition may contain additives other than the inactive diluent such as adjuvant e.g. wetting agents and suspending agents, sweeteners, flavors, fragrance and preservatives.

The composition of the present invention may be in the form of sprays which contains one or more active ingredients and may be prepared according to a known method.

Examples of the injectable compositions of the present invention for parenteral administration include sterile aqueous or nonaqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. These are sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

Another formulation of the composition according to the present invention may be rectal or vaginal suppository. Said suppository may be prepared by mixing at least one active compound according to the invention with a suppository base e.g. cacao butter and may optionally be admixed with a nonionic surfactant to improve absorption.

The term "treatment" used herein refers to any means of control of a condition including prevention, care, relief of the condition, and arrestation or relief of development of the condition.

The apoptosis inhibitor composition of the present invention can be applied for treatment of a various diseases and conditions associated with apoptosis. For example, the composition may be useful for treatment of nerve cell death by ischemia after cerebral infarction or the like, malignant tumor, autoimmune disease such as lymphocytopenia caused by virus infection such as AIDS, Alzheimer's disease, inflammation and eye disorders caused by light irradiation such as photoretinitis.

The composition of the present invention may further be admixed with any of pharmaceutically active agents in so far as said agent is compatible with the purpose of the present invention.

EXAMPLE

The present invention will be illustrated in more detail by way of the following examples. These examples should not be used as any limitation of the present invention.

Test Example (1) Breeding Condition and Administration Method

SD strain rats (male, 11 weeks old) were continuously exposed to 1000 lux of light for 4 days. During the exposure of light, the test group animals were administered subcutaneously with a composition comprising 2-decarboxy-2-(2-carboxyethyl)-13,14-dihydro-15-keto-16,16-difluoro-20-ethyl-PGE, isopropyl ester of the following formula (IV) at the amount of 10 µg/kg of the active ingredient per single administration three times a day, for 4 days. The control group animals were administered subcutaneously the same volume of the vehicle.

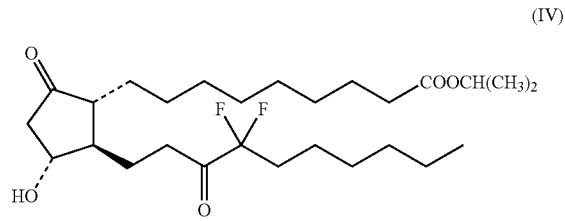

(2) Preparation and Staining

After the continuous light exposure was finished, animals of test and control groups were sacrificed by excessive etherization and both eyes of each animal were removed. The eyes were immediately fixed in a 2% paraformaldehyde and 2.5% glutaraldehyde solution in phosphate buffer, dehydrated with alcohol, and then embedded in paraffin. Thus fixed eyes were sliced parallel to the meridian of eye to provide thin retinal preparations each comprises optic disc. The obtained slices were subjected to tunnel staining (Apoptag® Intergen Company).

(3) Estimation

Total cell number and the number of tunnel-positive cells per 200 μm of the retina were counted and the ratio of the TUNEL-positive cells to the total cell number was determined.

(4) Result

The ratio of the TUNEL-positive cells is shown in table 1. The less number of positive cells means the stronger apoptosis inhibition.

TABLE 1

| | TUNEL-positive cell ratio | |
|---|---|---|
| | n | Ratio of the TUNEL-positive cells (%) (Ave ± SE) |
| Control group | 5 | 9.3 ± 0.8 |
| Test Group | 5 | 1.5 ± 0.2** |

**p < 0.01 (Mann-Whitney U-test)

The above result demonstrate the prostaglandin compound of the present invention has an apoptosis inhibiting activity.

INDUSTRIAL APPLICABILITY

The compound used in the present invention is useful as an apoptosis inhibitor. Therefore, said compound is expected to be useful in treatment or prophylaxis of a various conditions and diseases associated with apoptosis.

What is claimed is:

1. A method for treating photoretinitis in a subject in need thereof, which comprises administering an effective amount of a 15-keto prostaglandin compound represented by the following formula (II):

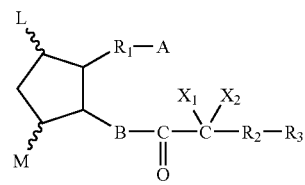

wherein L and M are hydrogen, hydroxy, halogen, lower alkyl, lower alkoxy, hydroxy(lower)alkyl or oxo, wherein at least one of L and M is a group other than hydrogen, and the five-membered ring may have one or more double bond;

A is —$CH_2OH$, —$COCH_2OH$, —COOH or its functional derivative;

B is —$CH_2$—$CH_2$—, —CH=CH— or —C≡C—;

$X_1$ and $X_2$ are hydrogen, lower alkyl or halogen;

$R_1$ is a divalent saturated or unsaturated lower-medium aliphatic hydrocarbon residue, which is unsubstituted or substituted by halogen, alkyl, hydroxy, oxo, aryl or heterocyclic group;

$R_2$ is a single bond or lower alkylene; and $R_3$ is lower alkyl, lower alkoxy, cyclo(lower)alkyl, cyclo(lower)alkyloxy, aryl, aryloxy, heterocyclic group or heterocyclic-oxy group to the subject.

2. The method of claim 1, wherein the 15-keto-prostaglandin compound is a 13,14-dihydro-15-keto-prostaglandin compound.

3. The method of claim 1, wherein the 15-keto-prostaglandin compound is a 15-keto-16-mono or dihalogen-prostaglandin compound.

4. The method of claim 1, wherein the 15-keto-prostaglandin compound is a 13,14-dihydro-15-keto-16-mono or di-halogen-prostaglandin compound.

5. The method of claim 1, wherein the 15-keto-prostaglandin compound is a 15-keto-16-mono or di-fluoro-prostaglandin compound.

6. The method of claim 1, wherein the 15-keto-prostaglandin compound is a 13,14-dihydro-15-keto-16-mono or di-fluoro-prostaglandin compound.

7. The method of claim 1, wherein the 15-keto-prostaglandin compound is a 15-keto-20-lower alkyl-prostaglandin compound.

8. The method of claim 1, wherein the 15-keto-prostaglandin compound is a 15-keto-20-ethyl-prostaglandin compound.

9. The method of claim 1, wherein the 15-keto-prostaglandin compound is a 2-decarboxy-2-(2-carboxy lower alkyl)-15-keto-prostaglandin compound.

10. The method of claim 1, wherein the 15-keto-prostaglandin compound is a 2-decarboxy-2-(2-carboxyethyl)-15-keto-prostaglandin compound.

11. The method of claim 1, wherein the 15-keto-prostaglandin compound is a 2-decarboxy-2-(2-carboxyethyl)-13,14-dihydro-15-keto-16-mono or di-fluoro prostaglandin compound.

12. The method of claim 1, wherein the 15-keto prostaglandin compound is a 2-decarboxy-2-(2-carboxyethyl)-13,14-dihydro-15-keto-16-mono or di-fluoro-20-ethyl-prostaglandin compound.

13. The method of claim 1, wherein the 15-keto prostaglandin compound is a 2-decarboxy-2-(2-carboxyethyl)-13,14-dihydro-15-keto-16,16-di-fluoro-20-ethyl-prostaglandin compound.

14. The method of claim 1, wherein the 15-keto prostaglandin compound is a 15-keto-prostaglandin E compound.

15. The method of claim 1, wherein the 15-keto prostaglandin compound is a 2-decarboxy-2-(2-carboxyethyl)-13,14-dihydro-15-keto-16,16-di-fluoro-20-ethyl-prostaglandin $E_1$ isopropyl ester.

16. The method of claim 1, which comprises administering ophthalmically a composition comprising a 15-keto-prostaglandin compound formulated in a dosage form suitable for ophthalmic administration.

17. The method of claim 16, wherein said composition is formulated as eye drops.

18. A method for treating light induced retinal photic injury in a subject in need thereof, which comprises administering an effective amount of a 15-keto prostaglandin compound represented by the following formula (II):

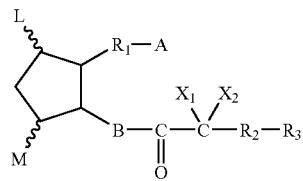

(II)

wherein L and M are hydrogen, hydroxy, halogen, lower alkyl, lower alkoxy, hydroxy(lower)alkyl or oxo, wherein at least one of L and M is a group other than hydrogen, and the five-membered ring may have one or more double bond;

A is —$CH_2OH$, —$COCH_2OH$, —COOH or its functional derivative;

B is —$CH_2$—$CH_2$—, —CH=CH— or —C≡C—;

$X_1$ and $X_2$ are hydrogen, lower alkyl or halogen;

$R_1$ is a divalent saturated or unsaturated lower-medium aliphatic hydrocarbon residue, which is unsubstituted or substituted by halogen, alkyl, hydroxy, oxo, aryl or heterocyclic group;

$R_2$ is a single bond or lower alkylene; and $R_3$ is lower alkyl, lower alkoxy, cyclo(lower)alkyl, cyclo(lower)alkyloxy, aryl, aryloxy, heterocyclic group or heterocyclic-oxy group to the subject.

* * * * *

UNITED STATES PATENT AND TRADEMARK OFFICE
CERTIFICATE OF CORRECTION

| | | |
|---|---|---|
| PATENT NO. | : 7,129,272 B2 | Page 1 of 1 |
| APPLICATION NO. | : 09/816655 | |
| DATED | : October 31, 2006 | |
| INVENTOR(S) | : Ryuji Ueno and Yukihiko Mashima | |

It is certified that error appears in the above-identified patent and that said Letters Patent is hereby corrected as shown below:

On the Title page item (60) should read: Provisional application No. 60/191,755, filed on Mar. 24, 2000.

Signed and Sealed this

Twenty-fourth Day of April, 2007

JON W. DUDAS
*Director of the United States Patent and Trademark Office*